(12) United States Patent
Gallant et al.

(10) Patent No.: US 10,463,527 B2
(45) Date of Patent: Nov. 5, 2019

(54) CONFIGURING ELASTIC SUPPORTS

(71) Applicant: Velcro BVBA, Deinze (BE)

(72) Inventors: Christopher M. Gallant, Nottingham, NH (US); Cynthia J. Oberg, Manchester, NH (US)

(73) Assignee: Velcro BVBA (BE)

( * ) Notice: Subject to any disclaimer, the term of this patent is extended or adjusted under 35 U.S.C. 154(b) by 808 days.

(21) Appl. No.: 15/000,167

(22) Filed: Jan. 19, 2016

(65) Prior Publication Data
US 2017/0202700 A1    Jul. 20, 2017

(51) Int. Cl.
*A61F 5/443*    (2006.01)
*A61F 5/44*    (2006.01)
*A61F 5/449*    (2006.01)

(52) U.S. Cl.
CPC ............ *A61F 5/4408* (2013.01); *A61F 5/443* (2013.01); *A61F 5/449* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 2,595,934 A | * | 5/1952 | Ginsburg | ............... | A61F 5/448 604/342 |
| 2,612,895 A | * | 10/1952 | Magee | .................. | A61M 27/00 604/327 |
| 2,778,362 A | * | 1/1957 | Pollock | ................... | A61F 5/445 604/345 |
| 2,788,785 A | * | 4/1957 | Present | ................... | A61F 5/445 604/345 |
| 3,773,048 A | * | 11/1973 | Kirkliauskas | ........... | A61F 5/445 604/345 |
| 4,347,843 A | * | 9/1982 | De Zaepffel | ............ | A61F 5/443 604/345 |
| 4,738,661 A | * | 4/1988 | Marut | ................... | A61F 13/148 128/DIG. 26 |
| 4,775,310 A | * | 10/1988 | Fischer | .............. | A44B 18/0049 425/308 |
| 5,260,015 A | * | 11/1993 | Kennedy | ............ | A44B 18/0003 264/167 |
| 5,300,037 A | * | 4/1994 | Delk | ..................... | A61M 25/02 128/DIG. 26 |
| 5,626,570 A | * | 5/1997 | Gallo | ...................... | A61F 5/449 2/49.2 |
| 5,865,820 A | * | 2/1999 | Myello | ................... | A61F 5/445 2/312 |

(Continued)

OTHER PUBLICATIONS

International Search Report and Written Opinion in International Application No. PCT/EP2017/050922, dated Apr. 6, 2017, 13 pages.

*Primary Examiner* — Tatyana Zalukaeva
*Assistant Examiner* — Guy K Townsend
(74) *Attorney, Agent, or Firm* — Fish & Richardson P.C.

(57) ABSTRACT

An ostomy belt has an elastic support membrane with a fibrous surface and an aperture for accessing a stoma. The aperture is formed by the user in a preferred location, and the area around the aperture is stabilized against stretch by applying a patch of relatively inelastic hook material to the fibrous surface about the aperture. An elastic membrane of an adhesive bandage is similarly stabilized about an opening in the bandage, by a hook patch that may have a flap for securing an IV tube.

14 Claims, 9 Drawing Sheets

(56) References Cited

U.S. PATENT DOCUMENTS

| | | | | |
|---|---|---|---|---|
| 5,918,599 | A * | 7/1999 | Shesol | A61M 16/0465 |
| | | | | 128/207.17 |
| 6,168,989 | B1 * | 1/2001 | Chiang | H01L 28/91 |
| | | | | 257/E21.019 |
| 6,296,164 | B1 * | 10/2001 | Russo | A61F 5/449 |
| | | | | 224/581 |
| 7,132,144 | B2 * | 11/2006 | Roberts | A44B 18/0073 |
| | | | | 428/40.2 |
| 7,166,091 | B1 * | 1/2007 | Zeltner | A61F 5/445 |
| | | | | 604/332 |
| 7,540,861 | B1 * | 6/2009 | Voto | A61F 5/443 |
| | | | | 604/343 |
| 7,661,152 | B2 * | 2/2010 | Manzano-Rivera | |
| | | | | A61M 25/02 |
| | | | | 2/114 |
| 7,935,097 | B1 * | 5/2011 | Moore | A61F 5/449 |
| | | | | 604/333 |
| 8,316,985 | B2 * | 11/2012 | Bain | A61F 5/441 |
| | | | | 181/198 |
| 2004/2061233 | | 12/2004 | Kingsford et al. | |
| 2007/0245449 | A1 * | 10/2007 | Ehmsen | A41B 9/004 |
| | | | | 2/109 |
| 2012/0283679 | A1 * | 11/2012 | Berish | A61F 5/449 |
| | | | | 604/345 |
| 2013/0261577 | A1 | 10/2013 | Brazeau | |
| 2014/0355910 | A1 | 12/2014 | Ferris | |
| 2015/0038927 | A1 | 2/2015 | Prody | |
| 2015/0065971 | A1 | 3/2015 | Goldsmith | |

* cited by examiner

CONFIGURING ELASTIC SUPPORTS

TECHNICAL FIELD

This invention relates to configuring or customizing elastic support membranes or bands of medical devices, such as ostomy belts.

BACKGROUND

Following abdominal surgery, some patients must wear ostomy pouches to collect waste fluids from a stoma extending through the abdominal wall. To prevent leakage, such pouches can connect to a patch adhered to the skin about the stoma. Ostomy belts are available that support the pouch and provide some elastic support to the abdomen, and have a hole through which the pouch connects to the adhered patch. The belt is worn such that the hole aligns with the stoma and the patch connection. Ostomy patients can have an increased risk of herniation about the stoma.

Some elastic bandages are also provided with openings through which a port or a wound can be accessed.

Improvements in these and other types of elastic bands or membranes, which provide access openings, are sought.

SUMMARY

Several aspects of the invention feature modifying or mitigating the stretchability of an elastic membrane about a hole or aperture in the membrane, by releasably securing to a fibrous surface of the membrane a relatively inelastic patch of hook fastener material, while leaving other areas of the membrane stretchable.

One aspect of the invention features a method of configuring an elastic support membrane having a fibrous surface. The method includes forming an aperture through the membrane at a selected location, such that the aperture is surrounded by the fibrous surface, and securing a stretch stabilizer to the fibrous surface of the membrane, the stretch stabilizer defining an opening at least mostly surrounded by a field of touch fastening elements that releasably engage with the fibrous surface of the membrane with the stretch stabilizer secured The formed aperture is aligned with the stabilizer opening to form a passage through the membrane, and the secured stretch stabilizer impedes stretch of the membrane in the vicinity of the formed aperture, while allowing an adjacent region of the membrane to stretch.

In some configurations the elastic support membrane is of a strap configured to couple to itself about living tissue, such as in the form of an abdominal belt. The strap may include a releasable buckle, a field of hooks configured to releasably engage fibers of the strap to secure the strap about living tissue.

In some configurations the elastic support membrane is of a bandage carrying adhesive, the method comprising adhering the bandage to living tissue at opposite ends of the membrane, thereby holding the membrane against the tissue.

In some embodiments the stretch stabilizer includes a layer of resin forming a surface of the stabilizer and forming, together with the touch fastening elements, a single, contiguous mass of resin.

For some applications, the method also includes forming a slit in the membrane running from the aperture to an edge of the membrane. The stretch stabilizer may include a flap positioned to extend across and close the slit in use, for example. The stretch stabilizer may include a flexible slit patch.

In some cases, the adjacent region of the membrane surrounds the stretch stabilizer.

In some configurations, the touch fastening elements are advantageously configured to snag fibers of the fibrous surface so as to allow for a gradual reduction in relative displacement between the fibrous surface and the stabilizer from an outer edge of the field of touch fastening elements toward the opening during stretch of the membrane.

The stretch stabilizer may include, or be in the form of, a flexible patch. In some implementations the patch comprises a flexible flap and the method includes, after securing the stretch stabilizer to the fibrous surface, securing a tube adjacent the aperture by folding the flap over the tube and securing a distal end of the flap to hold the tube in place.

The method may include, in some cases and prior to forming the aperture, selecting the location at which the aperture is to be formed. Prior to selecting the location at which the aperture is to be formed, the membrane may be positioned against living tissue to be supported. The stretch stabilizer may be secured after the location at which the aperture is to be formed is selected, and before the aperture is formed.

In some implementations the aperture is formed before the stretch stabilizer is secured. The stretch stabilizer may be secured over and to a stretched area of the membrane.

Another aspect of the invention features an ostomy support belt having an elastic abdominal support panel having a fibrous surface and defining an aperture therethrough for receiving a stoma. A removable stretch stabilization patch is releasably secured to the fibrous surface of the support panel about the aperture by a field of discrete touch fastening elements extending from the patch toward the fibrous surface of the support panel. The patch has a lower modulus of elasticity than the support panel in a direction along the length of the belt, and defines an opening aligned with the aperture of the support membrane.

In some examples the patch includes a flexible sheet of resin from which the touch fastening elements extend.

Preferably the patch is in the form of a flexible laminate having one broad surface carrying the touch fastening elements and having an opposite broad surface covered with a fibrous material. The patch may overlap itself as secured to the fibrous surface, with some touch fastening elements of the patch releasably engaging the fibrous material of the patch.

In some embodiments, the support panel defines a slit running from the aperture to an edge of the support panel, and the patch extends across the slit. The patch may include a flap that can be selectively secured to the fibrous surface of the support panel in use, and then selectively released from the fibrous surface to open the slit with a remainder of the patch remaining engaged with the fibrous surface.

The fibrous surface may be of a knit loop material, for example.

Another aspect of the invention features an elastic medical support band having an elastic support membrane with a fibrous surface and defining an aperture therethrough, and a removable stretch stabilization patch releasably secured to the fibrous surface of the support panel about the aperture by a field of discrete touch fastening elements extending from the patch toward the fibrous surface of the support panel. Notably, the patch has a lower modulus of elasticity than the support panel in a direction along the length of the band and defines through the patch an opening aligned with the aperture of the support membrane.

Some embodiments of the support band include adhesive positioned on a side of the support band opposite the fibrous surface. For example, the adhesive may be disposed in two areas at opposite ends of the support band.

In some cases the patch is in the form of a flexible sheet of resin from which the touch fastening elements extend.

The patch may be in the form of a flexible laminate having one broad surface carrying the touch fastening elements and having an opposite broad surface covered with a fibrous material. In some examples the patch overlaps itself as secured to the fibrous surface, with some touch fastening elements of the patch releasably engaging the fibrous material of the patch.

In some applications the support panel defines a slit running from the aperture to an edge of the support panel, and the patch extends across the slit. For example, the patch may have a flap that can be selectively secured to the fibrous surface of the support panel in use, and then selectively released from the fibrous surface to open the slit with a remainder of the patch remaining engaged with the fibrous surface.

In some configurations the patch has a flap that can be selectively released from the fibrous surface to extend about a device and then secured to the fibrous surface of the support panel to secure the device to the support panel.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
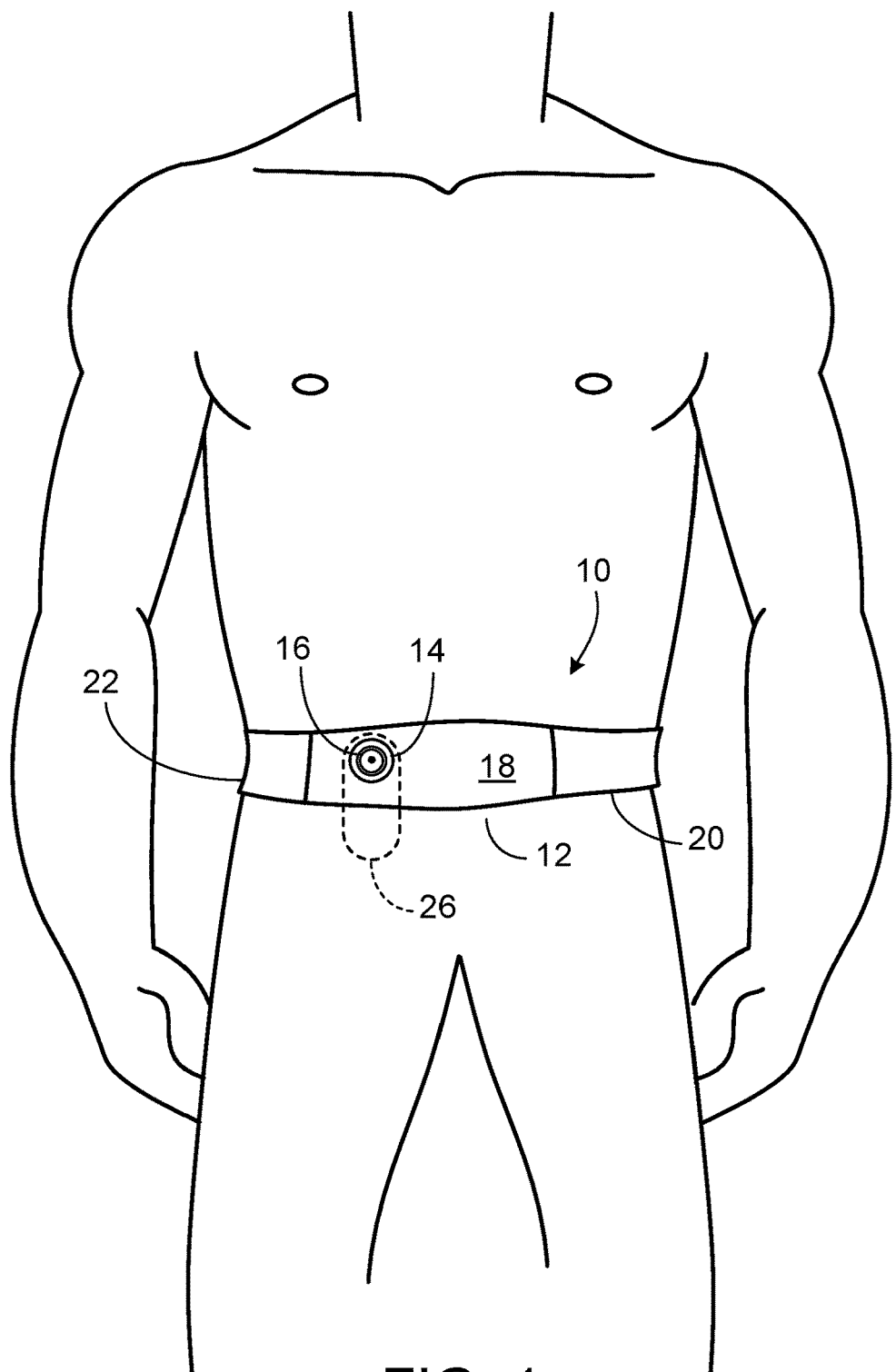
FIG. 1 shows an ostomy belt in use.
Figure 2:
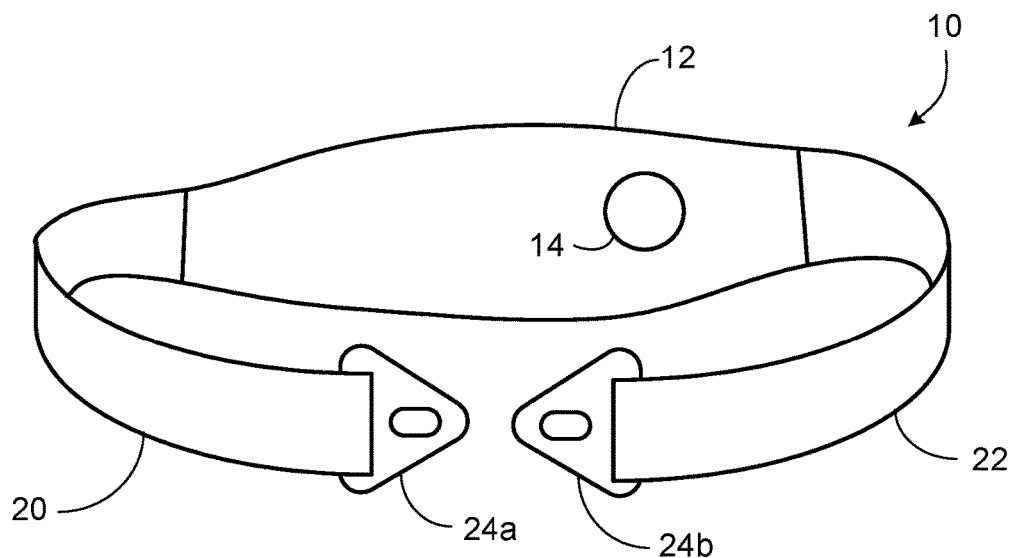
FIGS. 2 and 2A are rear views of two versions of the ostomy belt.
Figure 2A:
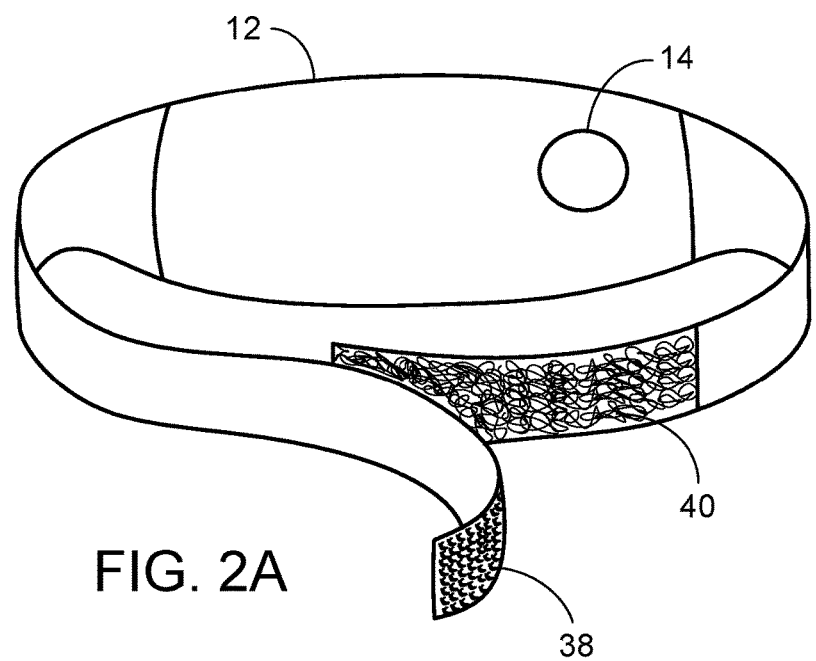

Referring first to FIGS. 1 and 2, an ostomy belt 10 has an elastic front panel or membrane 12 that, as worn, supports an abdominal wall of the wearer. Membrane 12 defines an aperture 14 exposing a stoma 16 extending from the wearer. Membrane 12 has a fibrous outer surface 18 formed of a textile material that extends between left and right belt ends 20 and 22 that encircle the wearer and are releasably connectable by buckle halves 24a and 24b. Thus, belt 10 is a strap configured to couple to itself about living tissue. As an alternative to a buckle, cooperating fields of hooks 38 and loops or engageable fibers 40 can be arranged to be overlapped at the ends of the belt when worn (as shown in FIG. 2A), to allow the belt to releasably engage to itself to hold the belt about the wearer. A similar fibrous or textile surface is provided on the inner side of belt 10, which is worn against the abdomen. Aperture 14 permits connection of an ostomy bag or pouch 26 to a connector of a patch adhered to the skin about the stoma, with the bag or pouch 26 worn outside belt 10.

Membrane 12 is elastic in the sense that it has a resilient stretchability in its plane, at least in the direction along the length of the belt (i.e., the direction extending across the wearer from side to side). The elasticity is sufficient to allow the membrane to stretch as the user moves, and to recover when relaxed. The belt is generally worn with membrane 12 in a somewhat stretched condition, such that it applies a continual pressure against the abdomen. Preferably, the membrane has a recoverable stretch percentage of between 20 percent and 150 percent in the direction of the length of the belt, measured as the change in length resulting from a static tensile force equivalent to 80 percent of a force sufficient to cause the membrane to yield, and from which change the membrane returns to less than 110 percent of its original length when relaxed. Membrane 12 is also of a width (top to bottom) sufficient to support a significant portion of the abdomen, preferably at least 75 mm in width. In this example the width is about 150 mm. The width should be sufficient to accommodate an aperture of the size required for ostomy pouch connection, with ample material surrounding the aperture.

Figure 3:
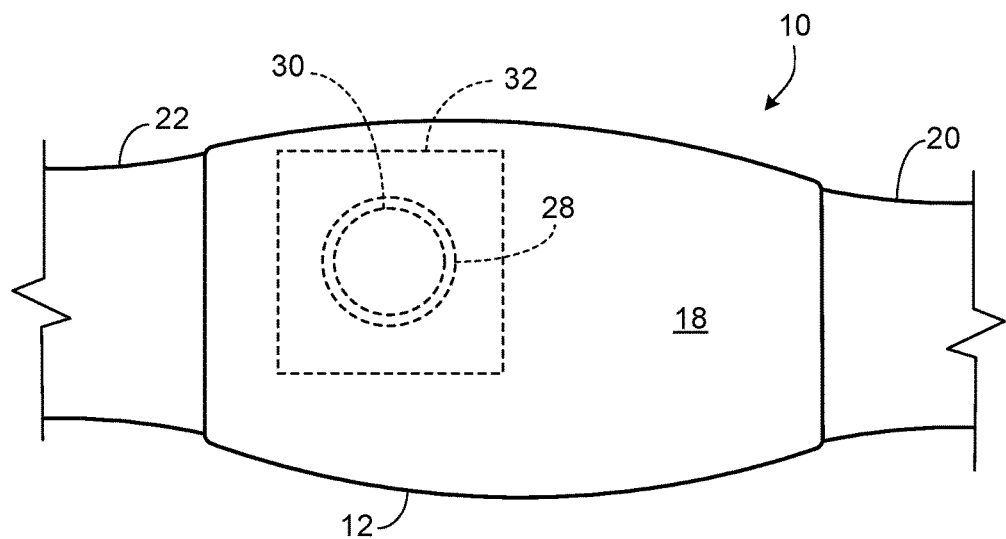
FIG. 3 shows the front of the ostomy belt before configuration.
Figure 4:
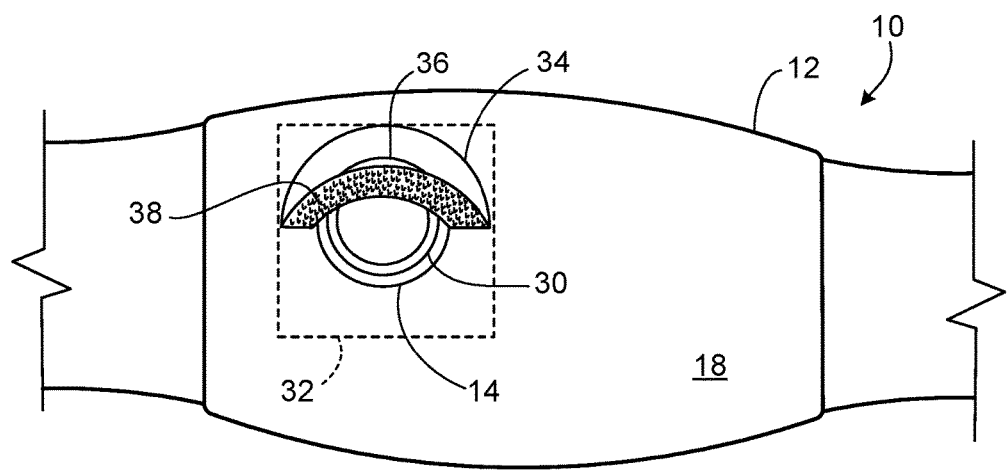
FIG. 4 shows a stretch stabilizer being applied to an outer surface of the ostomy belt about an aperture formed through the belt.

Referring to FIGS. 3 and 4, belt 10 is fashioned to be configurable to the particular location of a wearer's stoma. As provided (FIG. 3), the membrane 12 of belt 10 has no aperture. To configure the belt, the user first selects a location at which the aperture is to be formed, such as by donning the belt in a comfortable orientation and marking the location of the stoma. The user then forms the aperture, such as by cutting along a circular path 28 about the stoma location. The formed aperture should be of a sufficient size to expose a pouch connector 30 of a pouch attachment patch 32 worn about the stoma. In order to stabilize the elasticity of the cut membrane in the area about the aperture, the user applies a stretch stabilizer 34, in this case in the form of a flexible patch shown during installation with only the upper portion of the patch secured and the lower edge of the patch raised to show its inner surface. The stretch stabilizer defines an opening 36 that aligns with the formed aperture 14 to form a passage through the membrane, with the stretch stabilizer surrounding the aperture. As will be discussed further below, the stretch stabilizer has a field of touch fastening elements 38, such as hooks, extending from its inner surface so as to releasably engage the fibrous outer surface 18 of membrane 12 to secure the stretch stabilizer about the aperture as a reinforcement that reduces the net stretchability of the belt about the stoma aperture while allowing an adjacent region of the membrane to stretch. The installed stretch stabilizer adds little thickness to the overall belt and does not impede the connection of the ostomy pouch.

Figure 5:
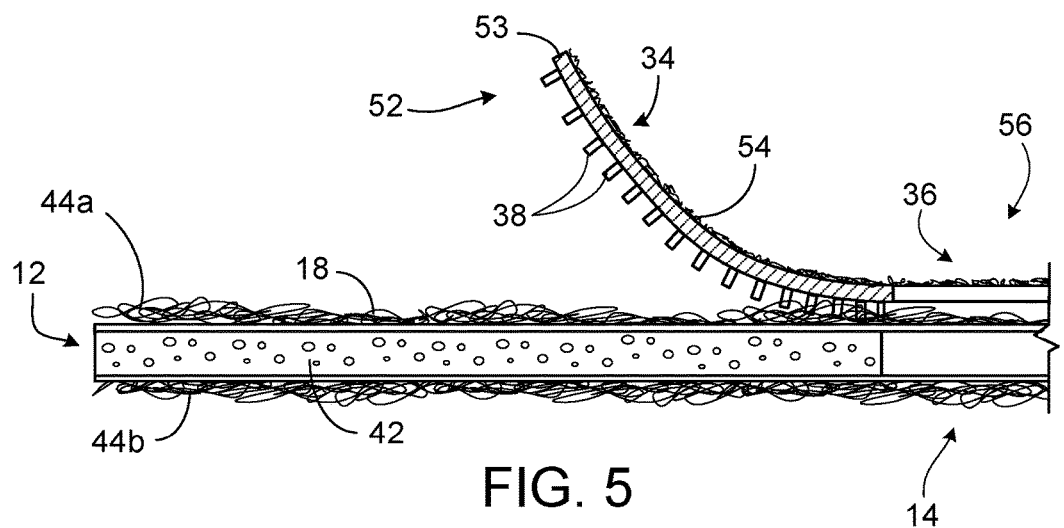
FIG. 5 is an enlarged, partial cross-sectional view, taken through a portion of the elastic membrane of the belt and the stretch stabilizer.
Figure 5A:
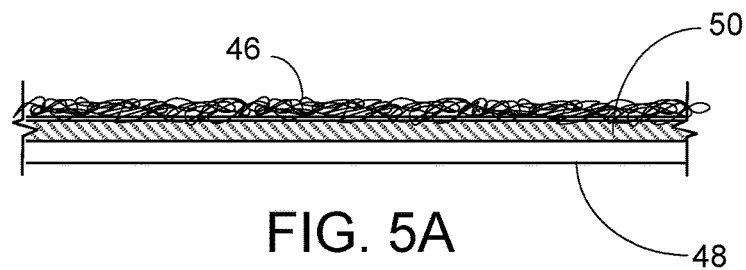
FIG. 5A is a cross-sectional illustration of an alternate membrane construction.

Referring next to FIG. 5, membrane 12 is an elastic laminate that has a foam core 42 sandwiched between textiles 44a and 44b. Textile 44a provides the fibrous outer surface 18 of the membrane, which features hook-engageable fibers of sufficient tenacity to withstand loads applied by the stretch stabilizer during use, without significant breakage. In this example, textiles 44a and 44b are both stretchable knit loop materials, such as those found in VELTEX brand loop laminates available from Velcro USA Inc. The foam core gives the membrane some resilience in its thickness, for added comfort. However, in another example shown in FIG. 5A membrane 12 is a simpler laminate consisting of a stretchable non-woven textile material 46 adhered to a stretchable film 48, either by a separate adhesive 50 or by solidifying the film directly on the back of the non-woven material. Referring back to FIG. 5, stretch stabilizer 34 is a flexible laminate of a sheet of plastic fastener material 52, which may be bonded to a textile backing 54. Fastener material 52 consists essentially of an inelastic resin base layer 53 of a thickness of, for example, 0.1 to 0.50 mm, and a field of fastening elements 38 individually extending from the base layer and forming, together with the base layer, a contiguous and seamless piece of resin. The touch fastening hooks can be of the J-hook, palm tree or mushroom type, or of any other type of projection configured to engage and retain fibers for fastening. Fastener material 52 can be formed from molten thermoplastic resin, such as polyethylene, in a continuous process, such as was disclosed by Fischer in U.S. Pat. No. 4,775,310, and can be formed to have textile backing 54, such as a non-woven having a basis weight of about 50-100 grams per square meter, embedded in the resin of the base sheet according to the process disclosed by Kennedy et al. in U.S. Pat. No. 5,260,015, the entire contents of both of which are incorporated herein by reference. For engaging a stretch knit material as discussed above, a suitable fastening element is CFM108, CFM29 or CFM85, available in several configurations from Velcro USA Inc. Textile backing 54 can itself have hook-engageable fibers exposed on the outer surface of the stretch stabilizer, such that the stabilizer can releasably engage itself if overlapped. FIG. 5 also illustrates the passage 56 formed by the aligned aperture 14 of membrane 12 and the opening 36 of the stretch stabilizer.

Figure 6:
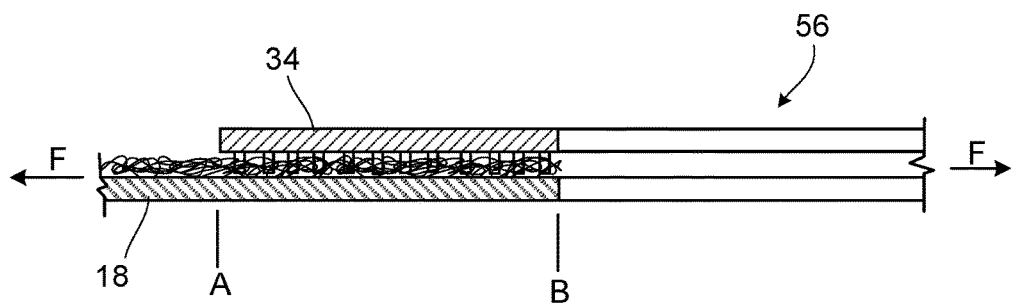
FIG. 6 shows a portion of an engagement between membrane and stabilizer during an elastic loading.
Figure 7:
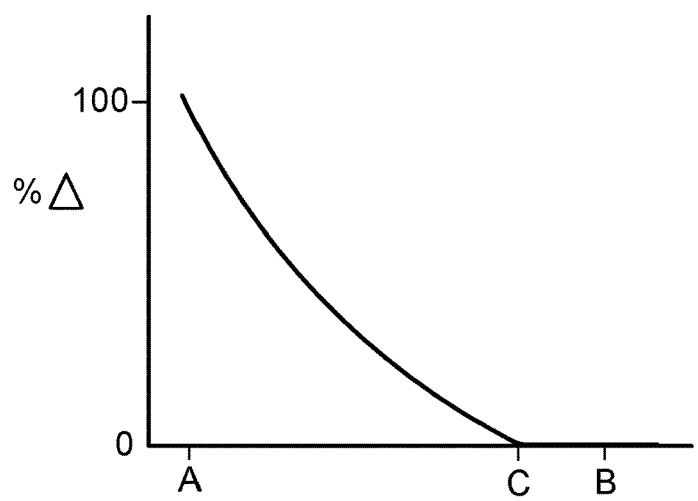
FIG. 7 illustrates a gradual reduction in net stretchability of the stabilized membrane across the engagement.

Referring next to FIGS. 6 and 7, the hook-loop engagement between membrane 18 and stretch stabilizer 34 provides a gradual reduction in elastic strain or displacement A over a distance from the outer edge (A) of the engagement to the inner edge (B) of the engagement at or near passage 56, as plotted schematically in FIG. 7 as a percentage of the strain rate of the exposed membrane (i.e., the portion of membrane not stabilized). Moving inward from outer edge (A), the net stretchability of the stabilized membrane is reduced as a function of distance from the outer edge, due to the limited movement within the fastening in the plane of stretch. This means that as the belt is subjected to longitudinal tensile force (F), the amount of stretch the stabilized membrane exhibits continually decreases from outer edge (A) until a point (C) where the stabilized membrane exhibits no appreciable stretch. The loop material and the field of fastening elements can be designed or selected so as to form a fastening of the desired amount of shear backlash under a given load, in order to position point (C) where desired. Generally, the lower the fastening backlash the closer to point (A) will be the point (C) of negligible stretch. Preferably there is a substantial width of relatively stretch-free support (i.e., the width from B to C) about passage 56. For a given membrane surface, different stretch stabilizers 34 can be provided with different arrangements and/or sizes/shapes of fastening elements in order to provide different levels of stretch resistance. The field of fastening elements of the stretch stabilizer can be arranged to cover the entire inner surface of the patch, or can be arranged to cover only particular regions configured to provide the desired amount and arrangement of stretch resistance. For many applications, (C) will be closer to the outer edge (A) of the fastening than to the inner edge (B). The less abrupt transition in stretchability provided by the limited slip of the hook-loop interface is believed to help avoid stress concentrations in the membrane that might otherwise develop at the outer edge of the stretch stabilizer, and can in some cases reduce local distortion of the membrane.

The stretch stabilizer can be applied to the membrane with the membrane in a relaxed condition, prior to donning the belt and inducing longitudinal stretch. Alternatively, the stabilizer can be secured about the aperture with the membrane already in a stretched condition, in which case the stretch stabilizer will work to stabilize the membrane in that condition and resist both further stretching and relaxing of the portion of the membrane immediately about the aperture. While it is preferred that the stretch stabilizer be essentially inelastic along the length of the belt (i.e., in the direction of anticipated elastic strain), it is sufficient for many applications that the stretch stabilizer merely has a lower modulus of elasticity than the membrane 12 in that direction.

Figure 8:
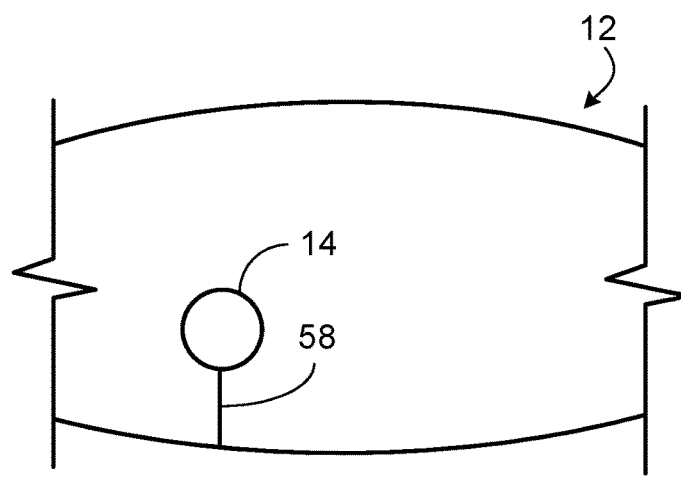
FIG. 8 shows a membrane configured to have both an aperture and a slit.
Figure 9:
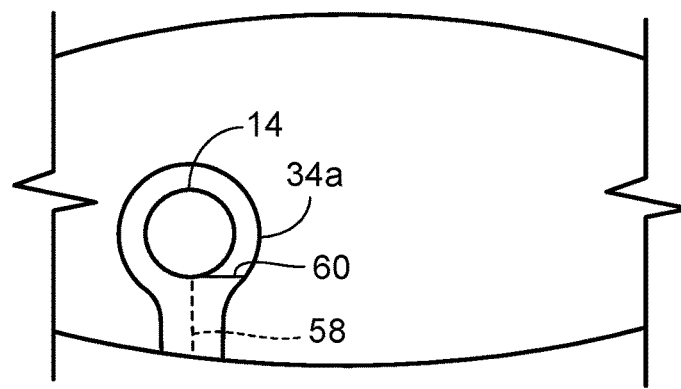
FIG. 9 shows the slit membrane of FIG. 8 with a stabilization patch applied.
Figure 10:
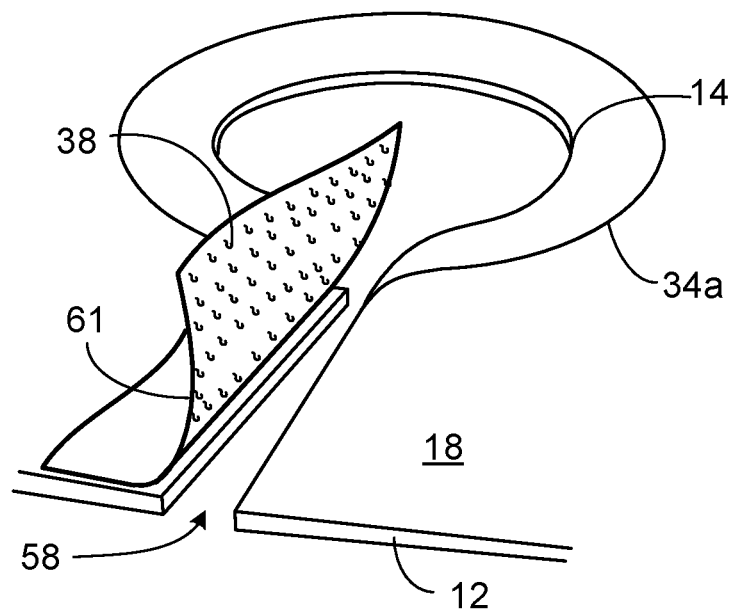
FIG. 10 illustrates folding back a flap of the patch of FIG. 9 to expose the slit.

Referring next to FIGS. 8-10, in another example of configuring an elastic ostomy belt for use, membrane 12 is cut from the formed aperture 14 to an outer (upper or lower) edge of the belt, forming a slit 58. A keyhole-shaped stretch stabilizing patch 34a is then secured to the fibrous surface of the membrane about the aperture and over slit 58, as shown in FIG. 9. Patch 34a has a slit 60 extending from its outer edge to its opening, such that the portion of the patch covering slit 58 forms a flap 61 that can be peeled back (FIG. 10) to allow slit 58 to be opened, such as for positioning the belt under an ostomy pouch that is already secured to the abdomen. The patch flap, which carries some of the fastening elements 38, can then be repositioned against the outer fibrous surface 18 of the membrane on the opposite side of slit 58, to secure the slit closed.

As noted above, the exposed outer surface of the stretch stabilizer can itself feature hook-engageable loops or fibers, and can thus be overlapped to be secured to itself in some configurations. The fibrous outer surface of the stabilizer can also function to help secure an ostomy pouch by engagement of a field of touch fastening elements of the pouch with the outer stabilizer surface.

Figure 11:
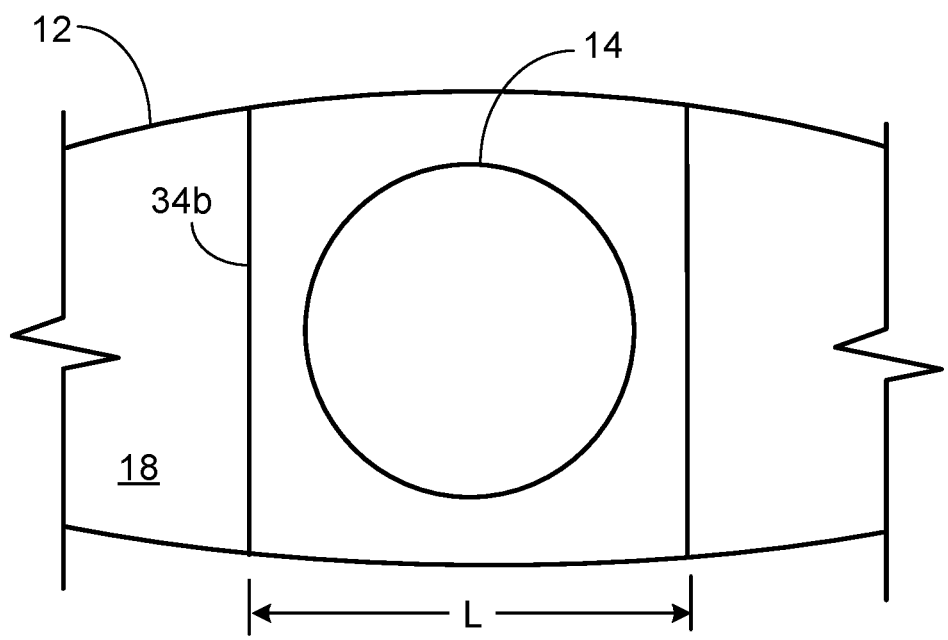
FIG. 11 shows an ostomy belt with a stretch stabilizing patch extending a full width of the belt.

While the above examples feature stretch stabilizers or patches that do not extend across the full width of the belt membrane, leaving at least sections of the width fully stretchable in use, FIG. 11 features a full-width stretch stabilizer 34b that extends across the elastic membrane from top to bottom to cover the membrane over a longitudinal distance (L) in which the stretchability of the membrane is mitigated. Stabilizer 34b can be positioned over whatever longitudinal section of belt is to be stabilized, and an aperture 14 formed through the membrane, or through both the membrane and the stabilizer, where needed.

Figure 12:
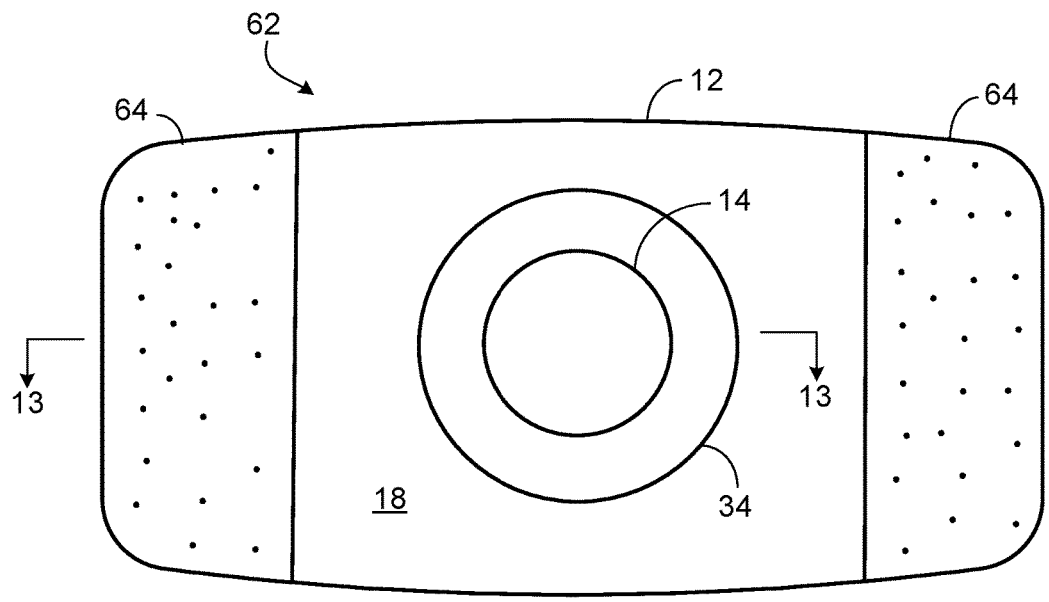
FIG. 12 is a top view of an elastic bandage with an engaged stretch stabilizer.
Figure 13:
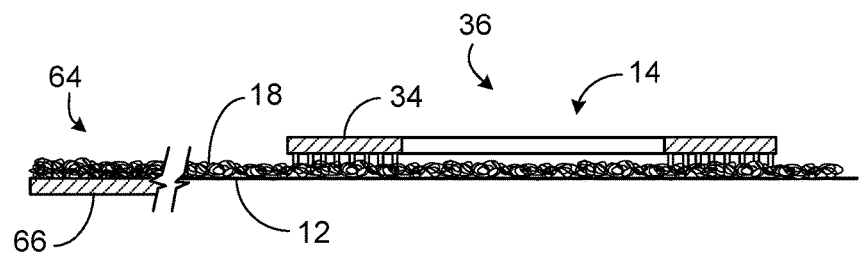
FIG. 13 is a cross-sectional view, taken along line 13-13 in FIG. 12.

Referring next to FIGS. 12 and 13, a bandage 62 has an elastic membrane 12 with relatively inelastic adhesive wings 64 at either end. Membrane 12 has no adhesive on either side, but has a fibrous outer surface 18 and may also have a fibrous inner surface. Membrane 12 defines an aperture 14 which is aligned with the opening 36 in stretch stabilizer 34 to form a passage, either for accommodating tubes or the like, or for providing access to an underlying wound or injection site. As in the ostomy belt example described above, stretch stabilizer 34 is a flexible patch with a field of fastening elements that releasably engages with the outer surface of the bandage membrane to mitigate the stretchability of the membrane in the area immediately about aperture 14. Adhesive 66 on an underside of the adhesive wings 64 secures the bandage to skin in use. The bandage can be secured in a stretched or relaxed position, and the stretch stabilizer can be secured to the membrane surface either with the membrane relaxed or with the membrane already in a longitudinally stretched condition.

Figure 14:
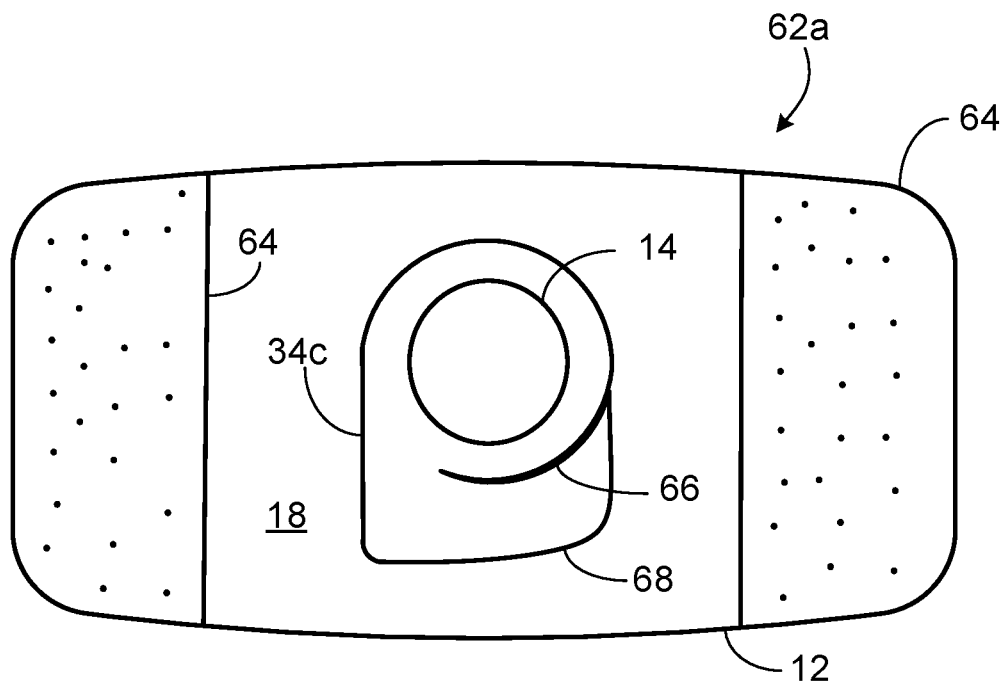
FIGS. 14-16 sequentially illustrate securing an IV tube to an elastic bandage stabilized with a patch having an IV tube flap.
Figure 15:
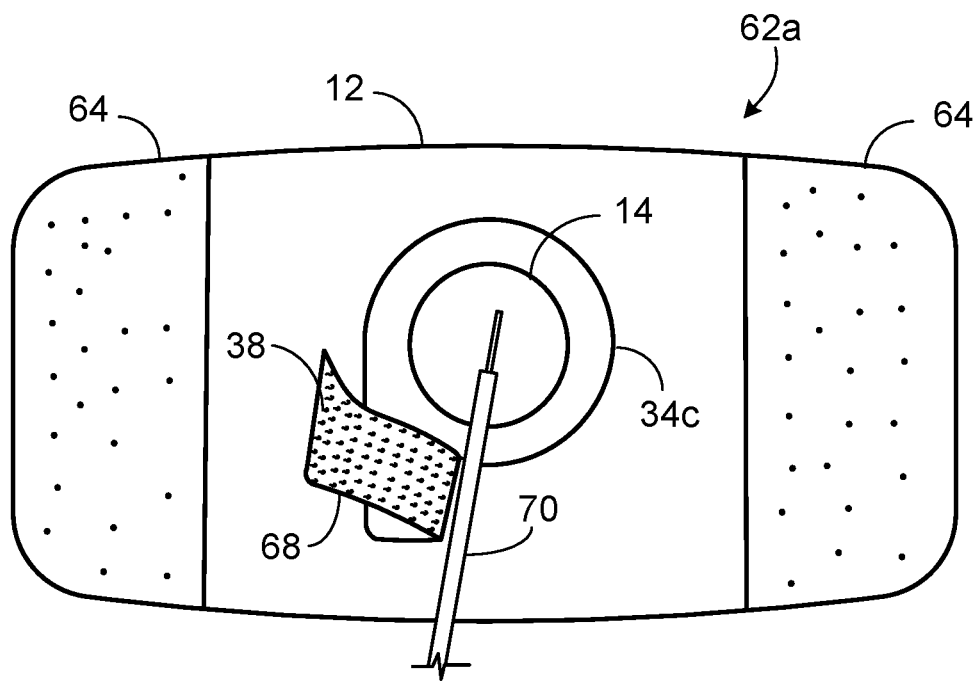
Figure 16:
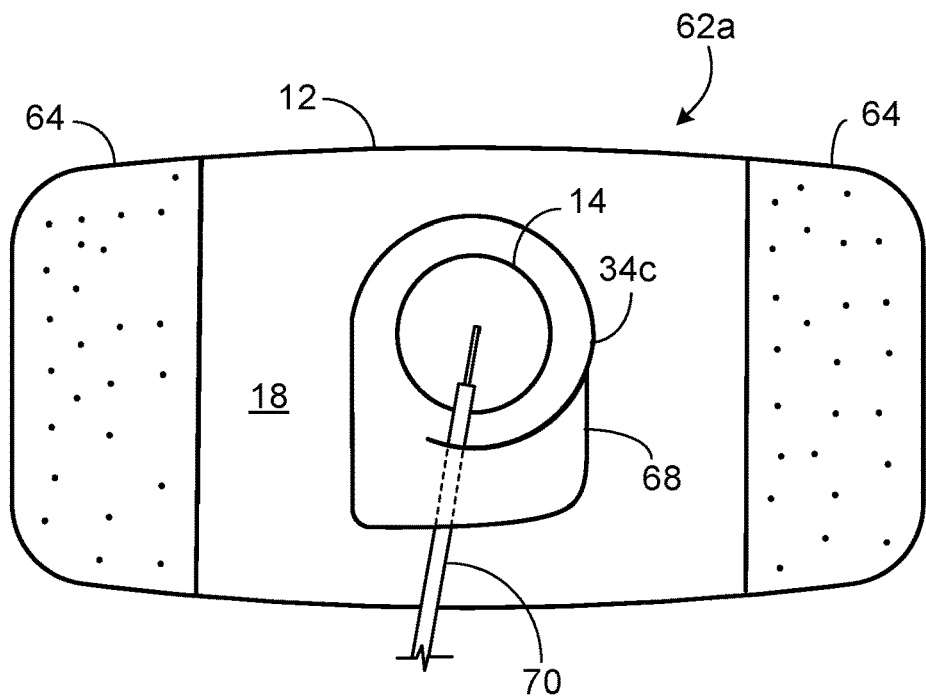

Referring next to FIGS. 14-16, a bandage 62a is similar to the one of FIGS. 12-13, but for the configuration of the stretch stabilizer. In this example the stretch stabilizer 34c has a slit that forms one edge of a flap 68 that can be peeled back from the fibrous surface 18 of the membrane 12, and then folded back in place over an IV tube 70 to hold the tube in place. In this manner stretch stabilizer 34c both stabilizes and reinforces the membrane about aperture 14 and forms an IV tube restraint.

Figure 17:
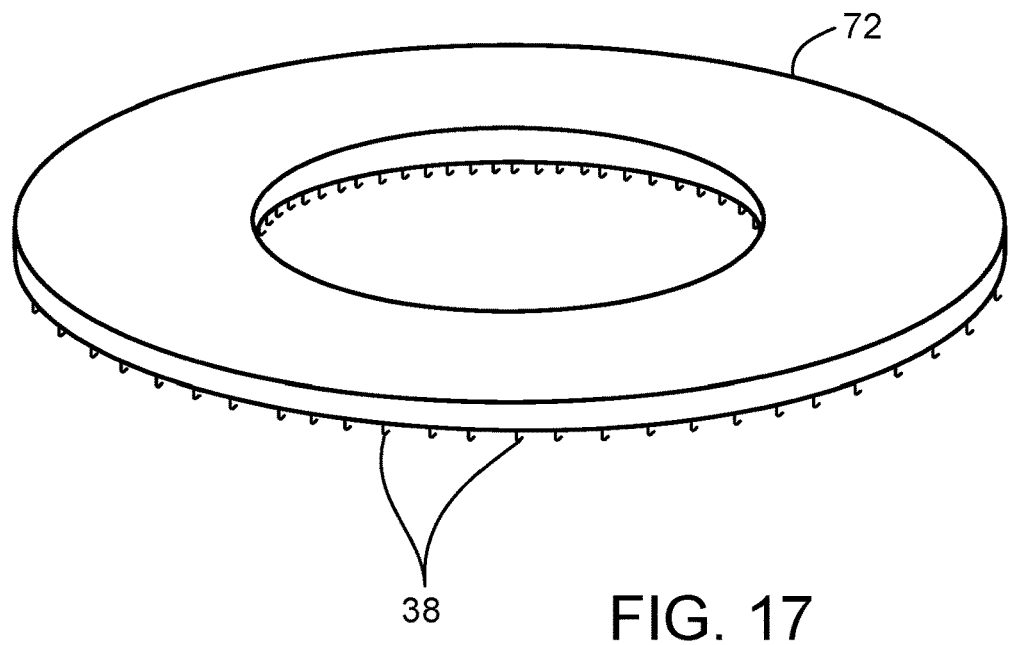
FIG. 17 illustrates a rigid stretch stabilizer.

While the above stretch stabilizers have been described and illustrated as flexible patches, for some applications a rigid stretch stabilizer may be suitable. FIG. 17 shows a rigid stabilization ring 72 formed as an injection molded structure having a field of touch fastening elements 38 molded to extend from a surface that engages against the fibrous surface of a stretchable membrane. Such a stretch stabilizer stabilizes the membrane against bending as well as against stretch at the border of the aperture.

While a number of examples have been described for illustration purposes, the foregoing description is not intended to limit the scope of the invention, which is defined by the scope of the appended claims. There are and will be other examples and modifications within the scope of the following claims.

What is claimed is:

1. A method of configuring an elastic support membrane having a fibrous surface, the method comprising
   forming an aperture through the membrane at a selected location, such that the aperture is surrounded by the fibrous surface; and
   securing a stretch stabilizer to the fibrous surface of the membrane, the stretch stabilizer defining an opening therethrough, the opening at least mostly surrounded by a field of touch fastening elements that extend from a surface of the stretch stabilizer and releasably engage with the fibrous surface of the membrane with the stretch stabilizer secured;
   wherein with the stretch stabilizer secured, the opening is aligned with the aperture to form an access passage through the membrane and the stretch stabilizer, with the secured stretch stabilizer impeding stretch of the membrane in the vicinity of the formed aperture while allowing an adjacent region of the membrane to stretch.

2. The method of claim 1, wherein the elastic support membrane is of a strap configured to couple to itself about living tissue.

3. The method of claim 2, wherein the strap is in the form of an abdominal belt.

4. The method of claim 1, wherein the elastic support membrane is of a bandage carrying adhesive, the method comprising adhering the bandage to living tissue at opposite ends of the membrane, thereby holding the membrane against the tissue.

5. The method of claim 1, wherein the stretch stabilizer comprises a layer of resin forming a surface of the stabilizer and forming, together with the touch fastening elements, a single, contiguous mass of resin.

6. The method of claim 1, further comprising forming a slit in the membrane running from the aperture to an edge of the membrane.

7. The method of claim 6, wherein the stretch stabilizer comprises a flap positioned to extend across and close the slit in use.

8. The method of claim 1, wherein the adjacent region of the membrane surrounds the stretch stabilizer.

9. The method of claim 1, wherein the touch fastening elements are configured to snag fibers of the fibrous surface so as to allow for a gradual reduction in relative displacement between the fibrous surface and the stabilizer from an outer edge of the field of touch fastening elements toward the opening during stretch of the membrane.

10. The method of claim 1, wherein the stretch stabilizer comprises a flexible patch.

11. The method of claim 10, wherein the patch comprises a flexible flap, the method comprising, after securing the stretch stabilizer to the fibrous surface, securing a tube adjacent to the aperture by folding the flap over the tube and securing a distal end of the flap to hold the tube in place.

12. The method of claim 1, further comprising, prior to forming the aperture, selecting the location at which the aperture is to be formed.

13. The method of claim 1, wherein the aperture is formed before the stretch stabilizer is secured.

14. The method of claim 1, wherein the stretch stabilizer is secured over and to a stretched area of the membrane.

* * * * *